United States Patent [19]
Heller et al.

[11] Patent Number: 5,543,326
[45] Date of Patent: Aug. 6, 1996

[54] BIOSENSOR INCLUDING CHEMICALLY MODIFIED ENZYMES

[76] Inventors: Adam Heller, 5317 Valburn Cir., Austin, Tex. 78731; Ioanis Katakis, 1200 Mearns Meadow #208, Austin, Tex. 78758; Ling Ye, 3904 Coventry La., #2B, Mishawaka, Ind. 46543

[21] Appl. No.: 207,035

[22] Filed: Mar. 4, 1994

[51] Int. Cl.$^6$ .............................. C12M 1/40; C12M 1/34
[52] U.S. Cl. ...................... 435/287.9; 435/817; 204/403
[58] Field of Search ................................. 435/14, 25–28, 435/174, 176, 177, 180, 181, 188, 189, 190, 288, 291, 817; 204/153.12, 403

[56] References Cited

U.S. PATENT DOCUMENTS

| | | | |
|---|---|---|---|
| 4,206,286 | 6/1980 | Keyes | 435/176 |
| 4,619,754 | 10/1986 | Niki et al. | 435/817 |
| 5,262,035 | 11/1993 | Gregg et al. | 435/817 |
| 5,264,092 | 11/1993 | Skotheim et al. | 435/817 |
| 5,310,469 | 5/1994 | Cunningham et al. | 435/817 |

OTHER PUBLICATIONS

Rennke et al. "Chemical Modification of Horseradish Peroxidase" J. of Histochemistry and Cytochemistry. vol. 27, NdO (1979) pp. 1352–1353.

Electron Transfer Between Glucose Oxidase and electrodes via Redox Mediators Bound with Flexible Chains to the Enzyme Surface, Schuhmann, W.; Ohara, T.; Heller, A.; Schmidt, H.–L., J. Am. Chem. Soc., 113, 1395–1397 (1991).

Y. Yasusa et al, "Periodate Oxidation of Carbohydrate Moiety of Stem Bromelain without Much Alteration in Enzymatic Activity," Biochemistry, vol. 10, No. 13, 1971, 2624–30.

High Current Density "Wired" Quinoprotein Glucose Dehydrogenase, Ye, L.; Hammerle, M.; Olsthoorn, A. J. J.,; Schuhmann, W.; Schmidt, H. L.; Duine, J. A.; Anal. Chem. 65, 238–241 (1993).

A. De Baetselier etal, "Fermentation of a Yeast Producing A. Niger Glucose Oxidase: Scale–up, Purification and Characterization of the Recombinant Enzyme," June 1991.

B. Gregg et al, "Redox Polymer Films Containing Enzymes. 2. Glucose Oxidase Containing Enzyme Electrodes, " J. Phys. Chem., vol. 94, No. 15, 1991, 6976–5980.

L–$\alpha$–Glycerophosphate and L–Lactate Electrodes Based on the Electrochemical "wiring" of Oxidases, Katakis, I., and Heller, A., Anal. Chem., 64, 1008–1013 (1992).

P. Lay et al, "Pentaammineosmium(III) and Hexaammineosmium(III) Complexes," Inorganic Syntheses, vol. 24, edited by J. Shreeve et al, 1986. pp. 268, 292, 294.

S. Nakamura et al, "Effect of Periodate Oxidation on the Structure and Properties of Glucose Oxidase," Biochimica et Biophysica Acta. 445 (1976) 294–308.

E. Sawicki et al, "The 3–Methyl–2–benzothiazolone Hydrazone Test," Analytical Chemistry, vol. 33, No. 1, Jan. 1961.

*Primary Examiner*—William H. Beisner
*Attorney, Agent, or Firm*—Merchant, Gould, Smith, Edell, Welter & Schmidt

[57] ABSTRACT

Oxidoreductases are chemically modified so as to change their net charge at a given pH. Through such modification the adsorption of the enzymes on surfaces, their retention in similarly or oppositely charged polymer membranes and their binding with similarly or oppositely charged macromolecules, particularly redox macromolecules, is controlled. The modified enzymes, of which modified recombinant glucose oxidase is an example, are useful in biosensors, e.g. for glucose; as marker enzymes of antigens or antibodies in immunosensing; and as labels of nucleotide sequences in probes, e.g. for DNA nucleotide sequences.

15 Claims, 11 Drawing Sheets

BIOSENSOR INCLUDING CHEMICALLY MODIFIED ENZYMES

LIST OF CITATIONS

De Baetselier, A.; Vasavada, A.; Dohet, P.; Ha-Thi, V.; De Beukelaer, M.; Erpicum, T.; De Clerck, L.; Hanotier, J.; Rosenberg, S. *Biotechnol.* 1991, 9, 559.
Gregg, B. A.; Heller, A. *J. Phys. Chem.* 1991, 95, 5976.
Katakis, I.; Heller, A. *Anal. Chem.* 1992, 64, 1008.
Lay, P. A.; Sargeson, A. M.; Taube, H. In *Inorganic Syntheses;* J. M. Shreeve, Ed. J. Wiley: New York, 1986; Vol. 24; pp 293–95.
Nakamura, S.; Hayashi, S.; Koga, K. *Biochim. Biophys. Acta* 1976, 445, 294.
Sawicki, E.; Hauser, T. R.; Stanley, T. W.; Elbert, W. *Anal. Chem.* 1961, 33, 93.
Yasuda, Y.; Takahashi, N.; Murachi, T. *Biochemistry* 1971, 10, 2624.
Ye, L.; Hammerle, M.; Olsthoorn, A. J.; Schuhmann, W.; Schmidt, H.-L.; Duine, J.; Heller, A. *Anal. Chem.* 1993, 65, 238.

FIELD OF THE INVENTION

This invention relates to enzymes used in biosensors and immunosensors. It relates particularly to enzymes that contain oligosaccharides. Through a sequence of reactions the oligosaccharides are modified so as to change the isoelectric point of the enzyme and thereby its attractive or repulsive interaction with a charged natural or synthetic polymer at a given pH.

BACKGROUND OF THE INVENTION

Adsorption and binding properties of enzymes are important in controlling their retention in, or leaching from, films formed of polyelectrolytes such as polyanions and polycations. They are also important in controlling their binding to matrices, from which they may be eluted, or to which they may be anchored, and in controlling heir adsorption on surfaces to which they may be well attached, or from which they may be readily removed by rinsing. They are also relevant to controlling their reversible or irreversible binding with biological macromolecules, such as nucleic acids, and with non-biological macromolecules, whether in a homogeneous solution, or when immobilized on a surface. Controlled binding to, or expulsion from, surfaces is particularly relevant to assaying biochemicals and immunochemicals. By changing the adsorption or binding characteristics, one can improve selectivity, signal to noise ratio and signal stability in these assays.

The charge of an enzyme affects its adsorption on surfaces, absorption in films, electrophoretic deposition on electrode surfaces, and interaction with macromolecules when the surfaces, films or macromolecules contain covalently or coordinatively bound cations or anions. When the concentration of dissolved small ions, that have charges of an opposite sign to that of the enzyme at a given pH, is not particularly high, then electrostatic repulsion reduces adsorption on, absorption in, or binding to surfaces, films or macromolecules, when the charges of these and the charge of the enzyme are of the same sign. When their charges and the charge of the enzyme are of opposite signs, adsorption, absorption or binding are enhanced. It is, therefore, of importance in diagnostic and analytical systems utilizing enzymes to tailor the charge of the enzyme so as to enhance its adsorption onto a surface, its absorption or retention in a film, or its binding to a macromolecule that may be dissolved in a solution or in a film on a surface. In other cases the opposite is desirable, i.e. it is important to facilitate desorption, removal, or stripping of the enzyme from a surface or matrix by making its interaction with a surface, or dissolved or immobilized macromolecule, repulsive. For example, in films used in optical or electrochemical blood glucose analyzers, it is desirable to retain the enzyme glucose oxidase (GOx) or the enzyme recombinant glucose oxidase (rGOx) in a film. Furthermore, it is preferred that the film contain an anionic polymer, termed polyanion, because polyanions partially exclude anionic species that interfere with the assays, such as ascorbate or urate. The unmodified enzymes GOx and rGOx, that in the physiological range (7.3±0.7) are polyanions, are better retained in polycationic films. These interact, however, with anionic interferants attractively. The attractive interaction increases the rate of permeation of interferant through the film. This enhances the undesired interference by the interferant. If the enzyme is, however, converted into a cationic or positively charged macromolecule, termed a polycation, then the enzyme is better retained in polyanionic films, from which interferants are partially excluded.

Control of the binding or repulsion of an enzyme from a surface is particularly important in immunoassays. These depend on specific binding of antigens and antibodies and on the prevention of non-specific binding to other surfaces or macromolecules. Most immunoassays involve the use of marker-enzymes that are chemically, usually covalently, bound to either an antigen or to an antibody. In immunoassays it is important to prevent non-specific binding of the marker-enzyme. Such non-specific binding can be reduced by using as the marker an enzyme that, because of its charge, i.e. its being a polyanion or a polycation, repulsively interacts with a surface or macromolecule involved in the immunoassay, thus assuring that the dominant attractive interaction is that between the specific antigen and the specific antibody. Here control of the charge of the enzyme enhances the specificity of the method, e.g. of enzyme linked immunosorbent assay referred to as ELISA.

Enzymes are also used to mark nucleic acids, e.g. DNA. They are used to label sequences of nucleotides and thus determine the presence or absence of complementary sequences, or to quantify the amount of specific sequences in test samples. These tests are based on highly specific interactions of components of genetic information carrying matter. In these, the enzyme, that labels or marks a sequence of nucleotides, must not itself bind non-selectively to the nucleic acid that is being probed with the enzyme labeled nucleotide sequence. By making the interaction between the nucleic acid that is probed and the enzyme electrostatically repulsive, non-specific binding can be avoided.

SUMMARY OF THE INVENTION

To enhance either the attractive or repulsive electrostatic interactions of enzymes, their charge at a given pH is varied by their chemical modification.

Specifically, the number of amines per enzyme molecule, or the number of carboxylic acid functions per enzyme molecule, is chemically altered by reacting oligosaccharide or other polyol functions of enzymes. The added amines or carboxylic acids added are covalently bound. They are an integral part of the functioning enzyme molecule, being linked via covalent bonds to the protein of the enzyme.

In the pH range where enzymes usually function, most amines are protonated, forming ammonium cations, and most carboxylic acids are ionized, forming carboxylate anions. Thus, when multiple amines are incorporated in the enzyme structure it becomes more positive, i.e. polycationic; and when multiple carboxylic acid functions are incorporated, it becomes more negative, i.e. polyanionic. A measure of the change is the variation in the isoelectric point of the enzyme, pI, defined as the pH where the enzyme is neutral, i.e. where the number of its cationic or positive charges equals the number of its anionic or negative charges. Through chemical modification the pI of the enzyme is changed and thereby its interaction with surfaces, sorbing matrices, polyelectrolytes, hydrogels, immunoreagents, nucleic acids, synthetic macromolecules or natural macromolecules is also changed.

The enzymes that are chemically modified can be derived of organisms that evolved naturally. They are, however, preferably derived of organisms that were genetically engineered in order to produce enzymes containing an increased amount of oligosaccharide or other polyol bound to the protein. The term polyol, throughout this invention, is used to describe polyalcohols, usually sugars, their natural derivatives, and their condensation or polymerization products.

Oligosaccharides or polyols containing vicinal, i.e. neighboring, diols can be oxidized, under conditions where the enzyme retains at least part of its initial catalytic activity, to polyaldehydes. A preferred oxidizing agent is the periodate anion. Through controlling its concentration, that of the enzyme, the pH, the temperature and the duration of the oxidation reaction, the average number of aldehyde functions per enzyme molecule can be varied. The aldehyde functions are then further reacted. In the case of rGOx up to 60 aldehyde functions can be produced in each enzyme molecule, with the enzyme retaining at least one third of its initial activity.

In one route, leading to enzymes that are more polycationic, i.e. have a higher pI, the polyaldehydes are reacted with an amine to form Schiff bases. While these can be used as such, they are preferably converted to amines with a reducing reagent, such as sodium borohydride. Also preferably, polyamines, such as ethylene diamine, diethylene triamine, triethylene tetramine, tetraethylene pentamine, or pentaethylene hexamine, are used to form the initial Schiff bases. Through the use of polyamines a greater number of amines is incorporated per aldehyde and the pI is more rapidly raised. It was found that in the case of rGOx the number of amines added to each enzyme molecule ranged between 0 and 300 when tetraethylene pentamine was used.

Alternatively, when an increase in the number of carboxylic acids per enzyme molecule is desired, i.e. when the objective is to make the enzyme more polyanionic and thus lower its pI, then the aldehyde functions can be reacted to form a Schiff base with an amine having two ester functions which, after sodium borohydride reduction and hydrolysis, yield dicarboxylic acid functions. Here two carboxylic acid functions are added per amine. The aldehyde functions can also be directly condensed with an aminopolycarboxylic acid, such as glutamic or aspartic acid, to form Schiff bases which, after sodium borohydride reduction, add one amine and two or more carboxylic acid functions. Alternatively, the aldehyde functions can be directly oxidized to carboxylic acid functions.

The enzymes modified with multiple amines have added advantages. They are easier to immobilize on surfaces by crosslinking. Many common crosslinkers including di- and polyaldehydes, like glutaraldehyde, di- and polyisocyanates, di- and trichlorocyanuric acids and their derivatives, react rapidly with amines, particularly primary amines. The enzymes modified with multiple amines are also easier to bind, with preservation of enzyme activity, to surfaces of materials, such as beads used in columns for carrying out enzyme-catalyzed chemical processes; to membranes or other films in biosensors; to immunoreagents such as antigens or antibodies; and to nucleotide sequences. Binding is facilitated by the added amines in the most commonly practiced coupling reactions. Examples of these include coupling reactions where amides are formed between enzyme amines and carboxylic acid functions of the surface or reagent, e.g. involving an O-acylisourea from a carbodiimide reaction, or an N-hydroxy-succinimide, or other active ester; or where Schiff bases are formed between enzyme amines and aldehyde functions of the surface or macromolecule.

In applications in biosensors, of which electrochemical biosensors are an example, an enzyme modified to be highly polycationic can interact with an electron-relaying polyanion. When the two are coated on the surface of an electrode they form an adduct, that can be further immobilized by crosslinking, e.g. with a diepoxide or a polyaziridine. Electrons are now relayed from the polycationic enzyme via the polyanionic redox polymer to the electrode. The polyanion with which the modified polycationic enzyme is mixed can also be a polyanion without redox functions. In this case any diffusional redox mediator can be used, but preferably a cationic diffusional mediator and preferably one having a multiple positive charge in its oxidized state is used. Such diffusional mediators are, for example, derived of complexes of o-phenanthroline or 2,2'-bipyridyl with $Os^{2+/3+}$, or are cationic organic mediators having in their oxidized form a quinoid structure, like Nile blue, or have a phenazonium ring structure, like the N-methylphenazonium ion; or are ferrocene derivatives. Though any fast redox couple having a redox potential between $-0.1V$ versus the standard calomel electrode (SCE) and $+0..6V$ versus the same electrode can be used, it is preferred that the redox couple contain a cation and that the potential of the redox couple be in the $-0.05V$–$+0.3V$ (SCE) potential range.

In addition to synthetic diffusional redox couples also natural redox couples, the best known examples of which are $O_2/H_2O_2$ and oxidized cytochrome C/reduced cytochrome C, can be used.

The control of charge of the enzyme is also important in preventing or reducing the rate of fouling of enzyme electrodes of biosensors. When an oxidizing potential is applied to an electrode, then anions migrate to its surface. Polyanionic enzymes can thus foul the electrodes, because of deposition of electrically insulating enzyme-protein or glycoprotein on their surface. Such fouling is prevented when the enzyme is convened to a polycation.

The enzymes, when modified to increase or change their charge, whether having a net positive or a net negative charge, i.e. whether being polycations or polyanions, can be electrophoretically deposited on electrode surfaces to which an appropriate potential is applied. This allows also the selective deposition of enzymes onto electrodes, i.e. onto conducting surfaces poised at an appropriate potential. The modified enzymes can be electrophoretically deposited by themselves; or when covalently bound to other macromolecules; or when attractively interacting with, or when non-covalently bound to, a macromolecule; or they can be electrophoretically co-deposited with a macromolecule that is not bound to the enzyme, but has a net charge of a sign similar to that of the enzyme.

The chemically modified enzymes, whether polycationic or polyanionic, also offer advantages in the manufacture of enzyme electrodes and biosensors, because they can be electrophoretically deposited on electrode surfaces from solutions that also contain a polycationic or polyanionic redox polyelectrolyte. Upon the application of an electrical potential enzyme molecules and polyelectrolytes are electrophoretically codeposited reproducibly and in well controlled amounts onto electrode surfaces, to form catalytically active films.

Furthermore, when chemically modified enzymes are used, the electrophoretic codeposition with a polyelectrolyte is possible in a pH range, preferably pH4 to pH9, where the enzyme retains its activity.

When an enzyme modified to be more positive (polycationic) or more negative (polyanionic) is used in any of the applications proposed, including biosensors, immunoassays and immunoreagent labels, immobilized enzymes in catalytic reactors, or nucleotide sequence markers, it is necessary that the change in the pI upon chemical modification of the enzyme be substantial, i.e. that the enzyme, after chemical modification, have a greatly increased number of positive or negative charges. The minimum change in pI, measured in pH units, required to adequately enhance the desired attractive or repulsive interaction with a counter or similarly charged surface or macromolecule, is by two units, i.e. it is necessary to shift the isoelectric point by not less than two pH units to achieve a desired change in interaction. Thus, for example, if an enzyme is neutral in a pH3 solution and it is desired to reduce the negative or increase the positive charge of the enzyme, it is necessary to raise its point of electroneutrality, i.e. its pI, to pH5 or higher. It is, however, preferred that the change in pI, either up or down, be greater. It is thus preferred to shift the pI by at least 4 pH units and, most preferably, by 6 pH units or more. The most commonly used method for measuring the isoelectric point (pI) of an enzyme is isoelectric focusing. According to this method the enzyme is subjected to electrophoresis in a gel, wherein a known pH gradient has been established. The pH zone where the enzyme does not migrate either to the anode or to the cathode defines its isoelectric point.

BRIEF DESCRIPTION OF FIGURES

FIG. 11b shows the glucose-electrooxidation current resulting from the adsorption of an aminated recombinant glucose oxidase on an electrode modified as in FIG. 11a.

EXAMPLES

Example 1

Measurement of Isoelectric Points of Enzymes

Isoelectric focusing, to be referred to as IEF, was performed with a Multiphor II® apparatus and a Multidrive XL® power supply from Pharmacia LKB. A refrigerated VWR water bath was used to keep the plate temperature at 10° C. Agarose, Gelbond®, coomasie blue, Ampholines®, Pharmalyte®, glass plates and electrode wicks were purchased from Pharmacia, protein IEF standards used to monitor pH from Biorad, and plates were silanized with Sigmacote® from Sigma. The molds used resulted in gels of ≈0.3 mm thickness. The gels were 1% agarose, 2% ampholines (pH 2.5–9.5) and were left in a humidity chamber for at least 4 hours at 4° C. The electrophoretic conditions were voltage limited (500 V) for 600–700 Vh at which point focusing was complete. The samples were applied 4–4.5 cm from the cathode corresponding to pH ≈7.5. The gels were fixed, washed, dried, stained and destained according to standard methods. The pH was measured within 5 min. after each run with a surface electrode.

Figure 1:
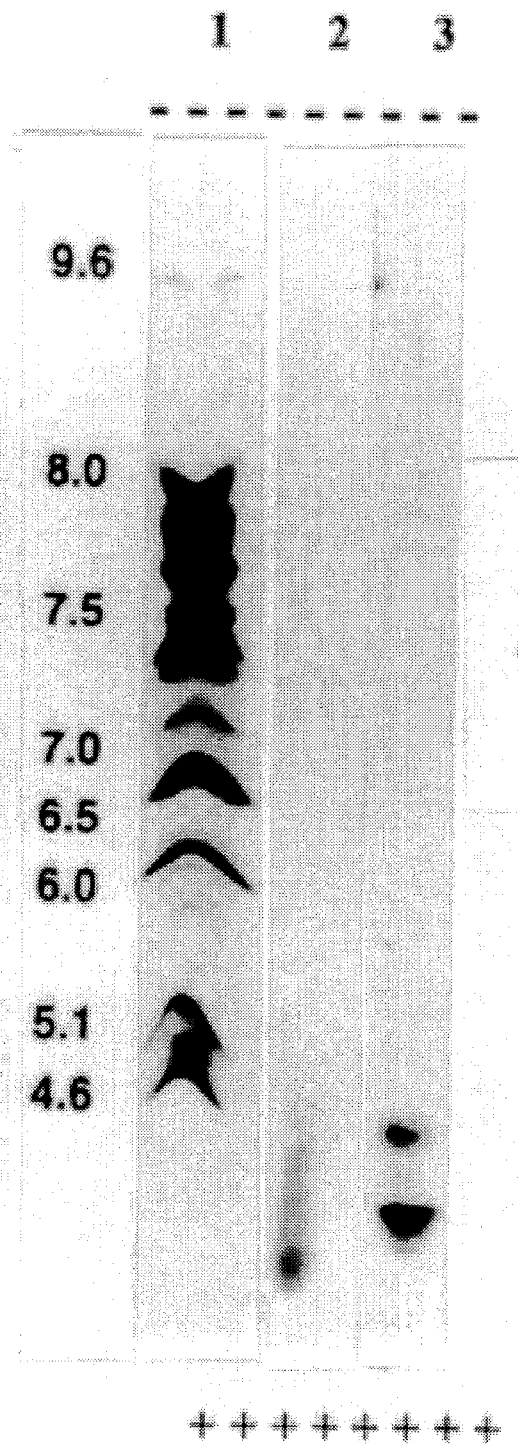
FIG. 1 shows that through isoelectric focusing the isoelectric point of enzymes can be measured.

FIG. 1 shows the electromigration behavior of recombinant glucose oxidase derived from yeast, referred to as rGOx, (lane 2) and of wild type glucose oxidase from Aspergillus Niger (Type X from Sigma), referred to as GOx, (lane 3). Lane 1 shows the migration of IEF standards, indicating the pH at any point in the gel. The arrow indicates the sample application point. As shown, the two enzymes have isoelectric points (pI) of approximately 3.5 (rGOx) and 4 (COx).

Example 2

Preparation of Modified Enzymes

Enzymatic Activity Assays and Protein Assays 2.4 mL oxygenated o-dianisidine (0.21 mM) in phosphate buffer (pH 7.3, 0.15M NaCl), 0.4 mL 2M glucose solution and 0.1 mL peroxidase (100 units $mL^{-1}$) were pipetted into a cuvette. After adding 50 μL of an rGOx or modified rGOx solution containing 0.05 mg enzyme $mL^{-1}$ and mixing by inversion, the increase of absorbance at 460 nm was recorded for 2 minutes. The enzymatic activity was calculated according to:

$$\frac{\text{units}}{\text{mg}} = \frac{\Delta A_{460}/\text{min} \times \text{Total Reaction Mixture Volume (mL)}}{11.3 \times \text{mg of Enzyme in Sample}}$$

The protein content of the sample was determined by measuring the absorbance at 280 nm and comparing it to the absorbance of samples for which the protein content was accurately known.

Peripheral Amination of rGOx

Figure 2:
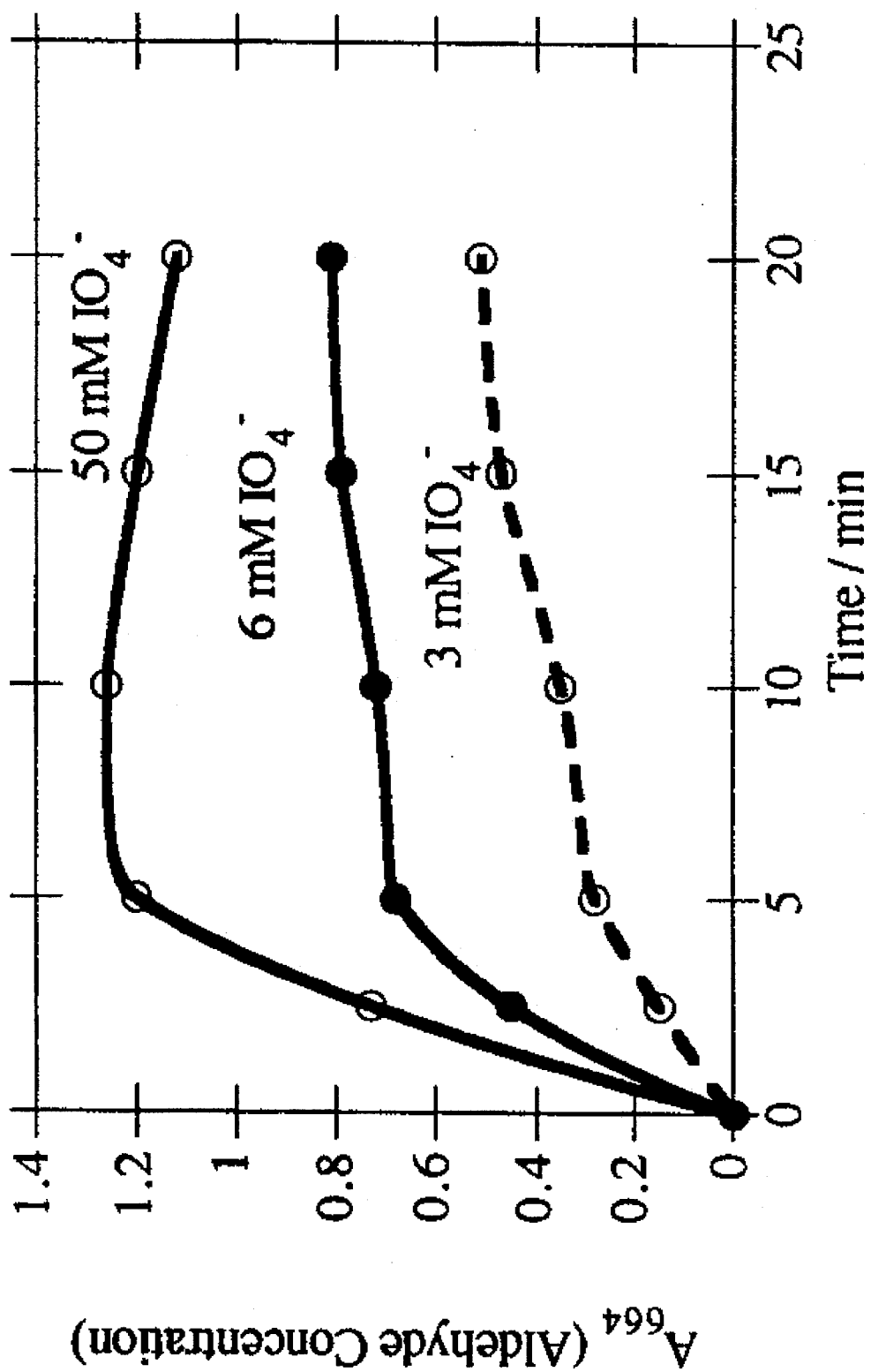
FIG. 2 shows the progress of the oxidation of the glycoprotein of recombinant glucose oxidase, termed rGOx, by periodate.

The oligosaccharide shell of Saccharomyces Cerevisiae rGOx (De Baetselier et al., 1991) was oxidized according to the procedure of Yasuda et al. (Yasuda et al. 1971, Nakamura et al. 1976). rGOx and $NaIO_4$ were dissolved in water and chilled to 4° C. in an ice-water bath. The reaction was started by adding an equal volume of $IO_4^-$ to the enzyme solution while stirring. The $IO_4^-$ concentration varied as indicated in Table 1. The progressive formation of aldehydes was monitored using the 3-methyl-2-benzothiazolone hydrazolone test (Sawicki et al. 1961) during the reaction by taking 25 mL aliquots of the reaction mixture at measured time intervals. FIG. 2 shows the change in absorbance resulting from production of aldehydes, indicating the progress of this reaction for three different initial concentrations of $NaIO_4$.

The oxidation reaction was stopped by adding 50 volume % ethylene glycol. The mixture was then dialyzed until the eluant was free of aldehyde and the enzyme solution was back to its original volume. The dialyzed enzyme solution was checked again for aldehyde content in order to determine the number of aldehydes on each enzyme molecule.

The aldehyde-enzyme solution was chilled to 4° C. After adding the same volume of pentaethylenehexamine solutions (of concentrations from 3 to 0.014M as indicated in Table 1), the reaction mixture was stirred for two hours to form Schiff bases, which were then reduced to secondary amines by reacting with an excess of sodium borohydride for 30 minutes. The enzyme solution was dialyzed with four times the volume of deionized water to reduce the amine and salt concentrations before it was further purified by gel filtration on a Sephadex G-150-120 column, eluted with 10 mM phosphate buffer, pH 6.5. The fractions with high specific activity were pooled and concentrated by ultrafiltration to the desired volume.

TABLE 1 shows the reaction conditions and products for several aminated rGOx variants.

Example 3

Preparation of Redox Polyelectrolytes

Cis-bis(2,2'-bipyridine-N,N')dichloroosmium(II), to be referred to as OsBpy, was synthesized according to the procedure of (Lay et al., 1986). In general the synthesis involved refluxing of $K_2OsCl_6$ with bipyridine in DMF for 1 hr, filtration of the precipitated KCl, and precipitation of the product in ether. The dark brown product was reduced with sodium dithionite, and characterized through its elemental analysis, UV spectrum and electrochemistry e.g. cyclic voltammetry. This material was used mainly for the derivatization of poly(vinyl pyridine), referred to as PVP, to synthesize the family of POs polymers as described below.

PVP-based redox polymers were synthesized with PVP, as the starting material. PVP was dissolved in methanol and recrystallized twice from ether. The molecular weight, as determined by HPLC, was 30 kDa.

Typically, the recrystallized material was refluxed with OsBpy for 1 h in the dark, under $N_2$, in about 20 mL of ethylene glycol for every 1 g of total solids. The polymer obtained, when the molar ratio of pyridines to OsBpy in the reaction mixture was 4:1, is referred to as PVPOs.

The synthetic procedure was similar to that reported earlier (Gregg and Heller, 1991; Katakis and Heller, 1992; Ye et al. 1993) with the following modifications; PVPOs was precipitated by slowly pouring the reaction mixture in vigorously stirred 1M NaCl aqueous solution. The fine precipitate was collected in a 2 μm nylon filter, dried, dialyzed extensively against water in Spectrapor® type 3 membranes (cutoff 3,500 Da) and characterized.

1 g of PVPOs and 1.5 g (7.3 mmol) of 2-bromoethylamine hydrobromide were heated overnight at 60° C. in the dark under $N_2$ in 50 mL DMF:ethylene glycol 3:2 v/v. The reaction product could be usually precipitated by the slow addition of the reaction mixture to rapidly stirred acetone (about 5 L). The precipitate was very hygroscopic and had to be collected in a 2 μm nylon filter. It was ion exchanged overnight with a 10 fold excess of chloride-form ion exchange beads (BioRad 1X-4), the beads were filtered and the eluent (in about 50 mL of water) was dialyzed extensively against deionized water. The final product, to be referred to as POs-EA, was precipitated again from acetone and characterized.

The same batch of PVPOs (0.9g) was used to synthesize the succinylated redox polyelectrolyte, to be referred to as POs-SA, by suspending PVPOs with 1.8 g of (±) bromosuccinic acid in 35 mL of 0.9M carbonate buffer. The final pH of the suspension was 6.35. The suspension was stirred under $N_2$ in the dark for 21 h at 68°–72° C. At this point the polymer dissolved and the solution cleared. The reaction product-containing mixture was precipitated by adding it to 1.5 L of rapidly stirred acetone. The precipitate (at this point containing most of the carbonate and bromide salts) was dissolved in acidified water (pH 4) and dialyzed against the same. The dialyzate was ion exchanged with chloride form ion exchange beads and redialyzed. The product was precipitated by slowly raising the pH of the solution to about pH 5, collected in a paper filter, and characterized.

Figure 3A:
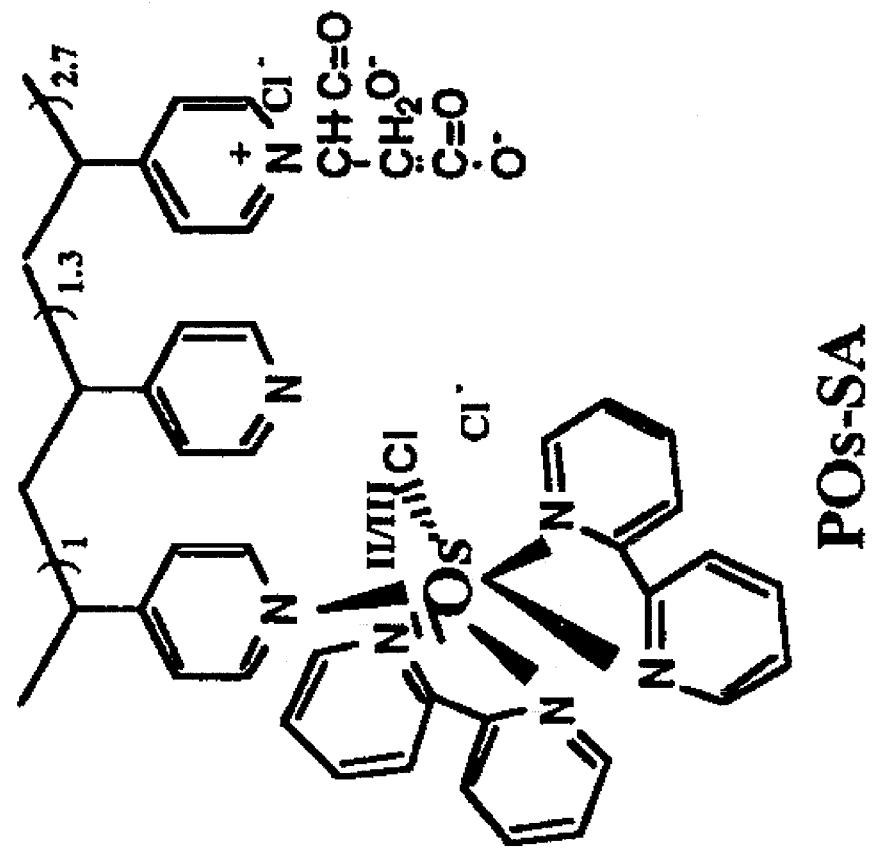
FIGS. 3a and 3b show structures of redox polyelectrolytes.
Figure 3B:
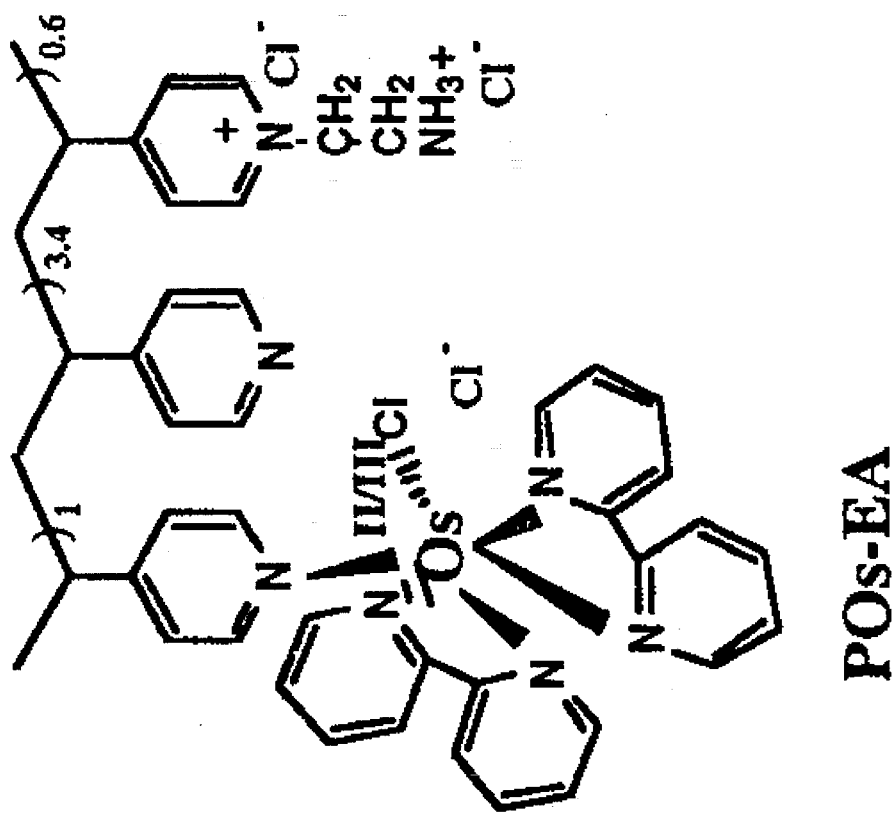

FIGS. 3a and 3b show the structures of the redox polyelectrolytes synthesized, as determined by elemental analysis and atomic absorption spectroscopy for osmium.

Example 4

IEF Characterization of Polyelectrolytes and Modified Enzymes

Figure 4:
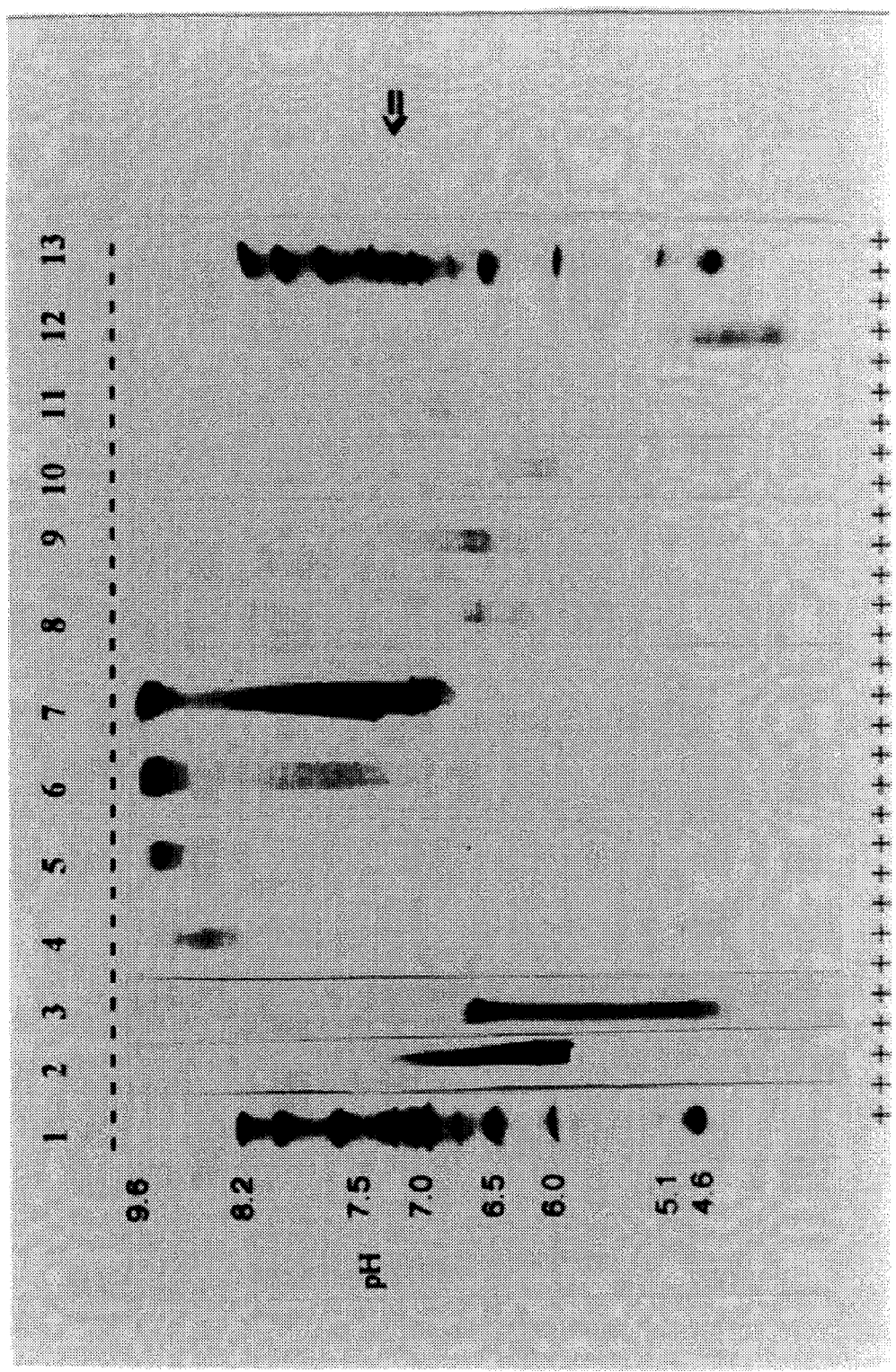
FIG. 4 shows isoelectric focusing and migration patterns of redox polyelectrolytes and of aminated recombinant glucose oxidase.

FIG. 4 shows the IEF runs of the synthesized polyelectrolytes and the modified enzymes. Lane 1 contains IEF standards. Lane 2, 15 mg POs-EA, lane 3, 15 mg POs-SA, lanes 4–11 the modified rGOx samples 1–8 of Table 1. Lane 12 is rGOx, and lane 13 again has IEF standards.

Example 5

Adduct Formation Between Modified rGOx and Redox polyelectrolytes

Figure 5:
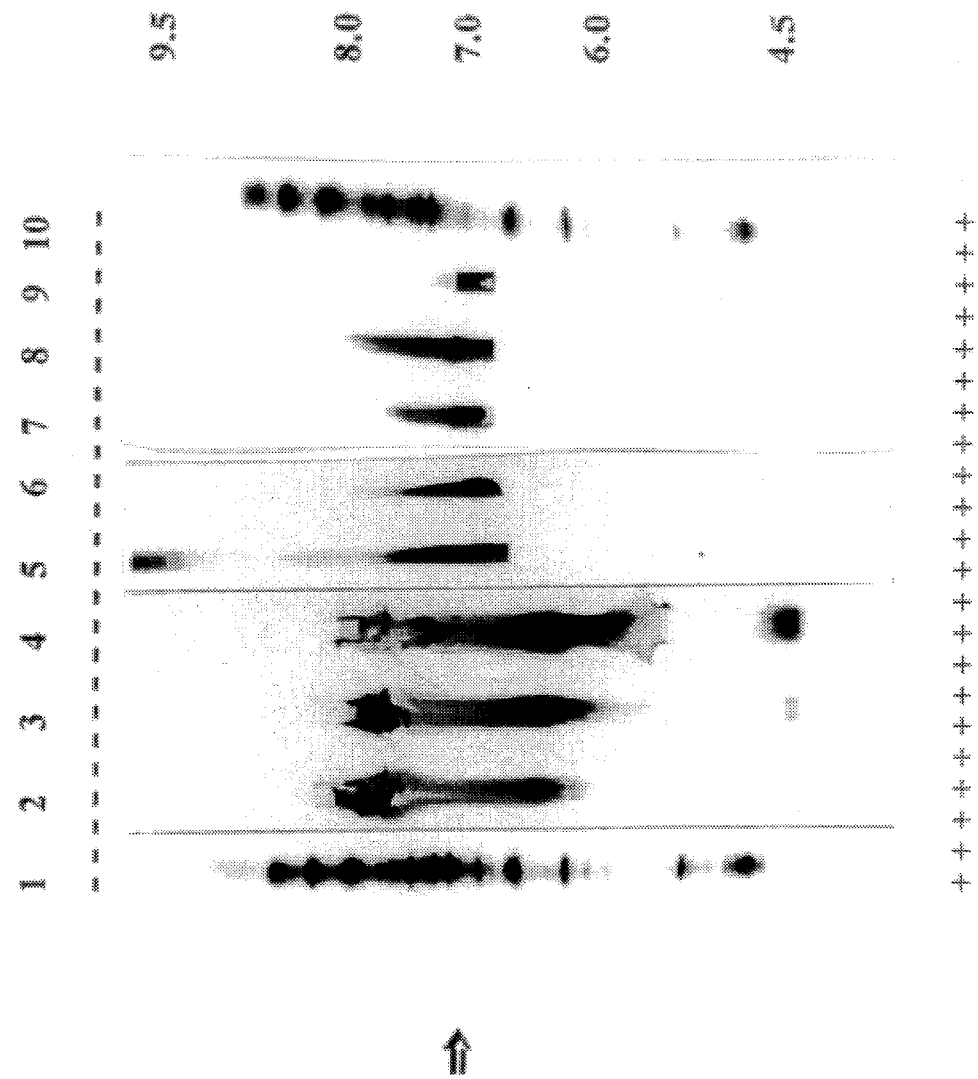
FIG. 5 shows, through isoelectric focusing, interactions of a polycationic redox polyelectrolyte with native recombinant glucose oxidase and two of its aminated derivates.

FIG. 5 shows IEF runs of mixtures of the polycationic redox polyelectrolyte with unmodified and several modified rGOx variants. For this gel, the polyelectrolyte and the enzyme were premixed and deposited on the agarose gel as per Example 1. Lane 1 shows IEF standards. Lanes 2–4 contain mixtures of rGOx with POs-EA with increasing weight % of rGOx as follows: 75, 77, 80 respectively. Lanes 5, 6 had mixtures of rGOx-9 i.e. of the product of reaction 2 of Table 1 with the POs-EA. The weight % of rGOx-9 in the mixture was 44% and 15% respectively. Lanes 7–9 had mixtures of rGOx-6 with POs-EA, rGOx-6 was the product of reaction 7 in Table 1. The weight % of rGOx-6 was 59, 42, 65 respectively. Lane 10 had IEF standards.

It can be seen in FIG. 5 that as the pI of the enzyme increases, the capacity of the polycationic redox polyelectrolyte to form an adduct with the enzyme is diminished (75% for rGOx with pI 3.5, ≈65% with rGOx-6 with pI 6, and ≈12% with rGOx-9 with pI of 9). The capacity of the polyelectrolyte to form an adduct is defined as the weight % of enzyme needed for the first trace of free enzyme to be detected on the agarose gel, the enzyme migrating independently of the adduct.

Figure 6:
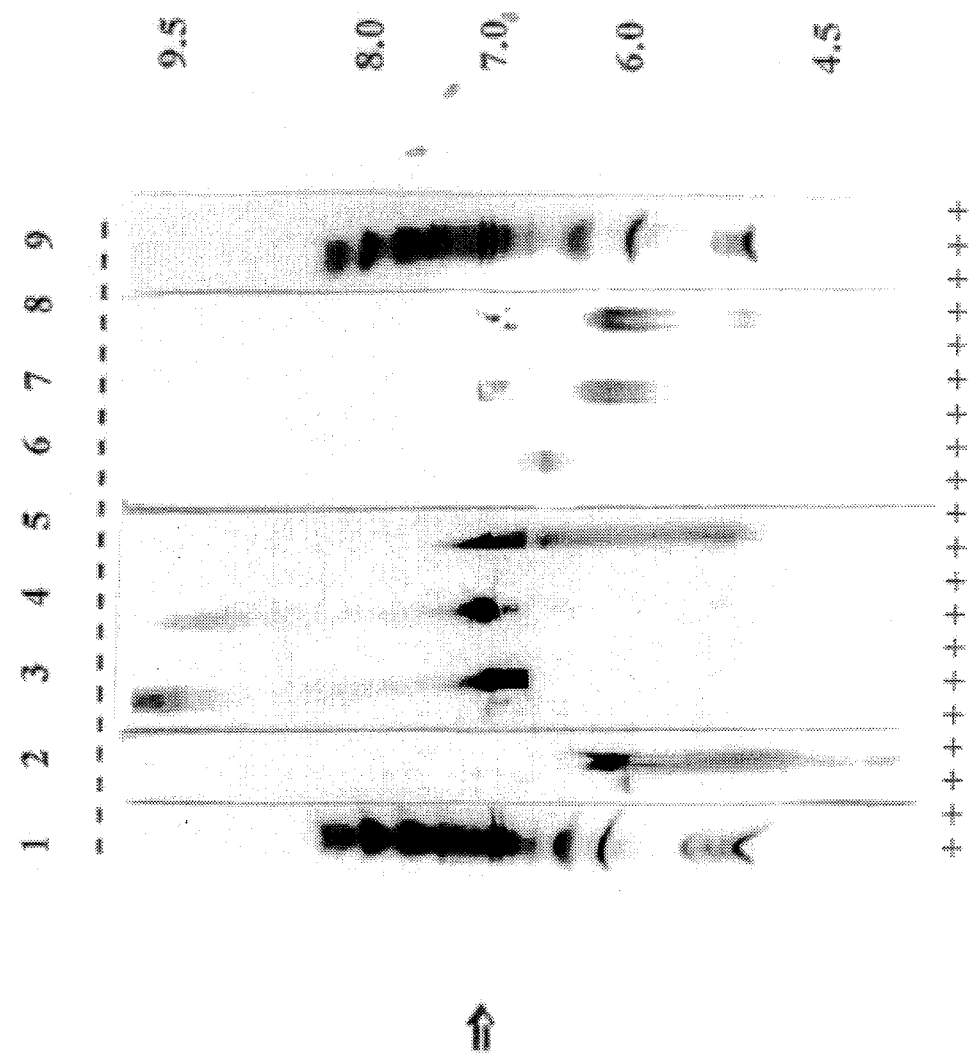
FIG. 6 shows the interactions of a zwitterionic-polyanionic redox polyelectrolyte with the enzymes of FIG. 5.

FIG. 6 shows IEF runs of mixtures of rGOx and its variants with the zwitterionic polyelectrolyte POs-SA. Lane 1 shows IEF standards. Lane 2 shows POs-SA with 10 weight % rGOx, lanes 3–5 show POs-SA with 62, 44, 29% weight rGOx-9, lanes 7,8 POs-SA with 42 and 26% weight rGOx-6, and lane 9 shows again the IEF standards. It can be seen in FIG. 6 that as the pI of the enzyme increases, the capacity of the overall anionic polyelectrolyte to form an adduct with the enzyme is increased (less than 10% for rGOx with pI 3.5, 30% with rGOx-6 with pI of 6 and 40% with rGOx-9 with pI of 9).

Example 6

Glucose Electrooxidation on Electrodes on which Redox Polyelectrolyte-Modified rGOx Adducts Were Adsorbed Electrochemical experiments were performed in 10 mL three-electrode electrochemical cells thermostated at 21° C. The cells were mechanically stirred at 1000 rpm and the solutions were saturated with argon. The reference electrode was saturated calomel electrode, referred to as SCE, and the counter electrode was a Pt wire. The working electrode was a 6.15 mm diameter spectrographic graphite rod, enclosed in heat-shrink tubing, with one side, forming a graphite disk, exposed to the solution. This disk was polished with sand paper and alumina slurry, sonicated, dried and then modified with $5 \pm 1 \times 10^{-8}$ moles cm$^{-2}$ of the redox polyelectrolytes. After thorough washing the electrode was poised at 0.45 V (SCE) and upon reaching a steady base line, solutions of the modified enzymes were injected. The solution was always 0.1M glucose in 0.033M phosphate buffer, pH 7.3 and 0.15M NaCl.

Figure 7:
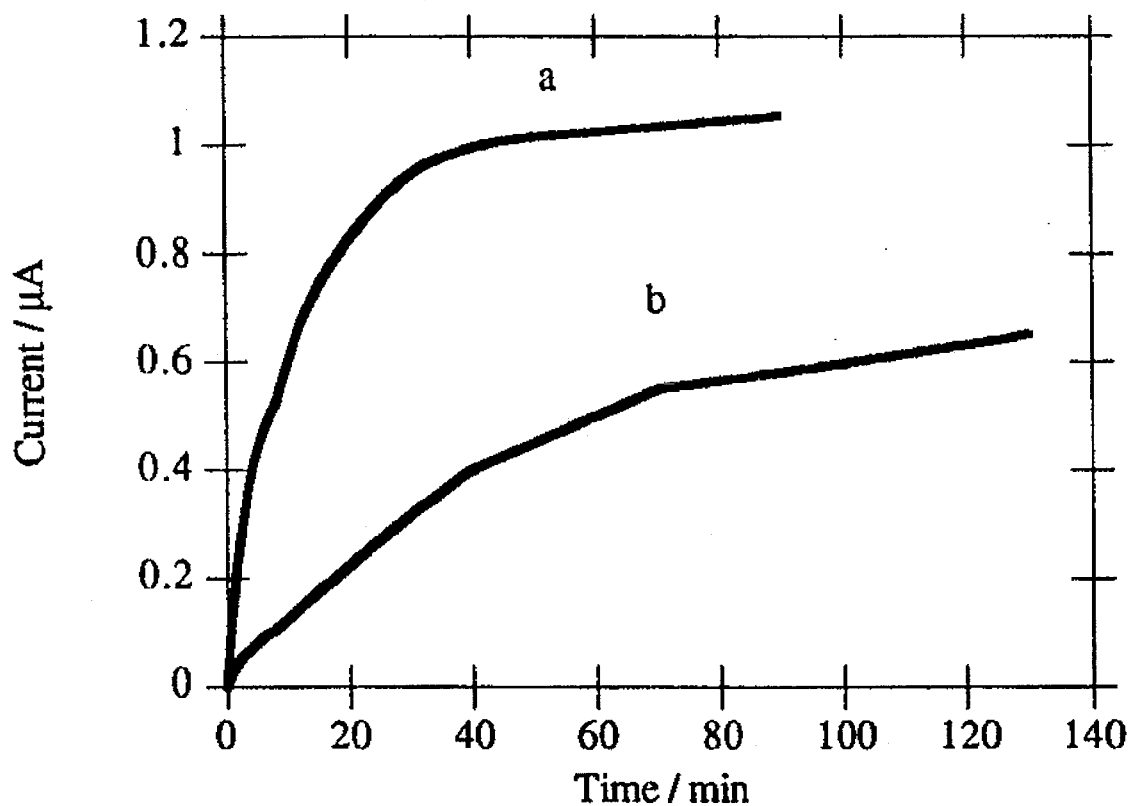
FIG. 7 shows the evolution of the glucose electrooxidation current when native or aminated recombinant glucose oxidase adsorb on electrodes modified with the polycationic redox polyelectrolyte.

FIG. 7 shows the response of an electrode modified with POs-EA to the injection of 3.1 mg mL$^{-1}$ or 0.43 units mL$^{-1}$ of rGOx (line a) and to 11 μg mL$^{-1}$ or 0.36 units mL$^{-1}$ of rGOx-9 (line b). It can be seen that as the pI of the enzyme increases, the adsorption to the polycationic polyelectrolyte-modified electrode and the rate of electron transfer from the enzyme to the redox polyelectrolyte is decreasing (at pH 7.3) and the current obtained is substantially smaller.

Figure 8:
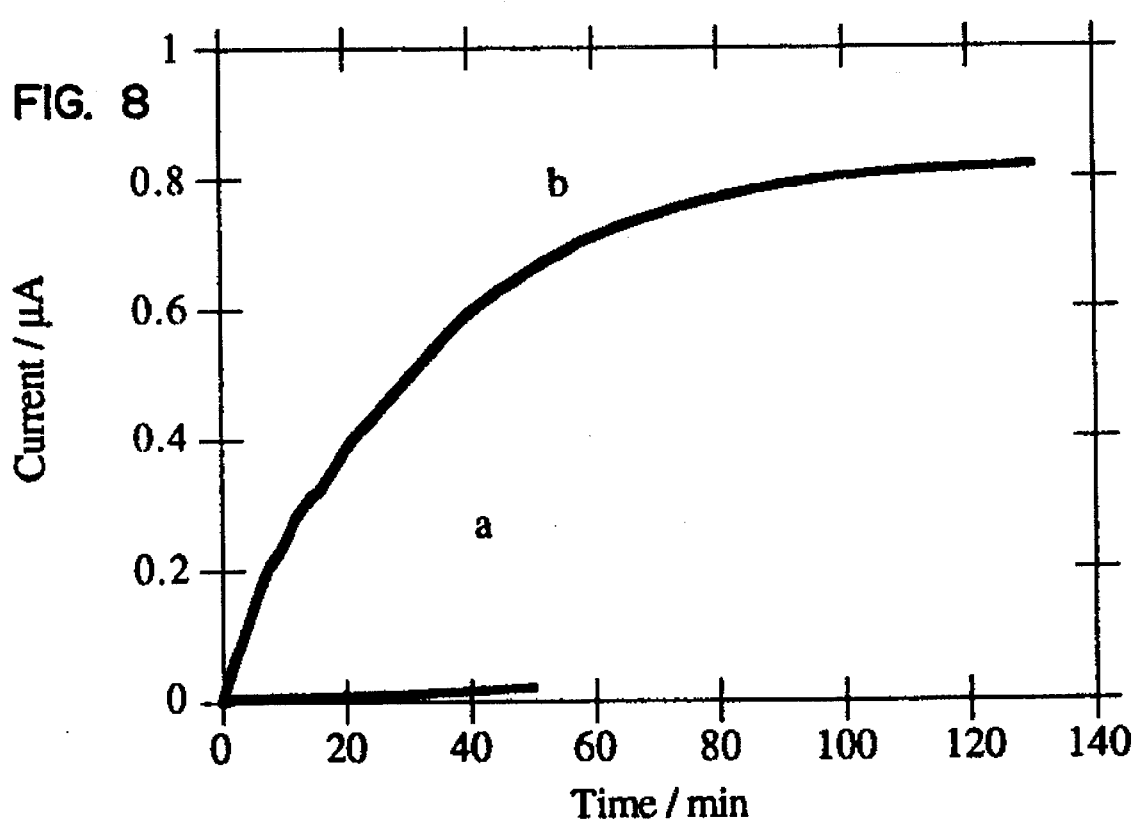
FIG. 8 shows an evolution similar to that of FIG. 7 for a zwitterionic-polyanionic redox polyelectrolyte adsorbed on the electrodes.

FIG. 8 shows the response of an electrode modified with POs-SA to the injection of the same amount of rGOx (line a) and rGOx-9 (line b) as used in the experiments of FIG. 7. It can be seen that as the pI of the enzyme increases, the adsorption on the polycationic polyelectrolyte-modified electrode and the rate of electron transfer from the enzyme to the redox polyelectrolyte increases (at pH 7.3) and the current is substantially higher.

Example 7

Enhancement of the Operational Stability in Enzyme Electrodes made with Modified rGOx The operational stability of amperometric enzyme electrodes was assessed by poising the rotating (1000 rpm) reagentless enzyme electrode (in this case glucose electrode) at 0.45 V vs. SCE in an Ar-swept phosphate buffer solution containing the enzyme's substrate. Reagentless enzyme electrodes were constructed by depositing on the electrode surface 2 μL of enzyme:redox polyelectrolyte:crosslinker solution and letting it cure for 24 hours. In the case of POs-EA the crosslinker was PEG and in the case of POs-SA it was PAZ. In the former case the weight % content of the electrode-modifying solution was 45% enzyme, 45% redox polyelectrolyte, 10% PEG and in the latter case the respective percentages were 40, 40 and 20. The current of enzyme electrodes deteriorated with time, possibly because of (a) enzyme leaching from the crosslinked film as a result of insufficient crosslinking and (b) electrophoretic migration of the negatively charged redox enzyme towards the electrode surface, resulting in fouling and loss of electrical contact between the redox polyelectrolyte and the electrode.

Figure 9:
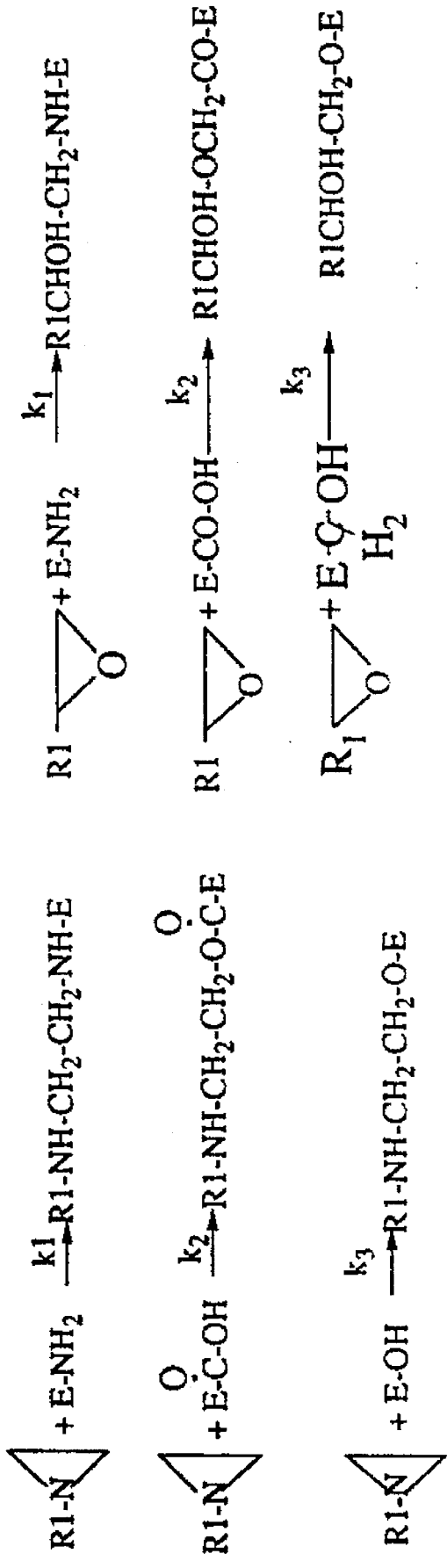
FIG. 9 shows structures of two common crosslinkers used in making electrocatalytic films on enzyme electrodes and their crosslinking reactions.
Figure 10:
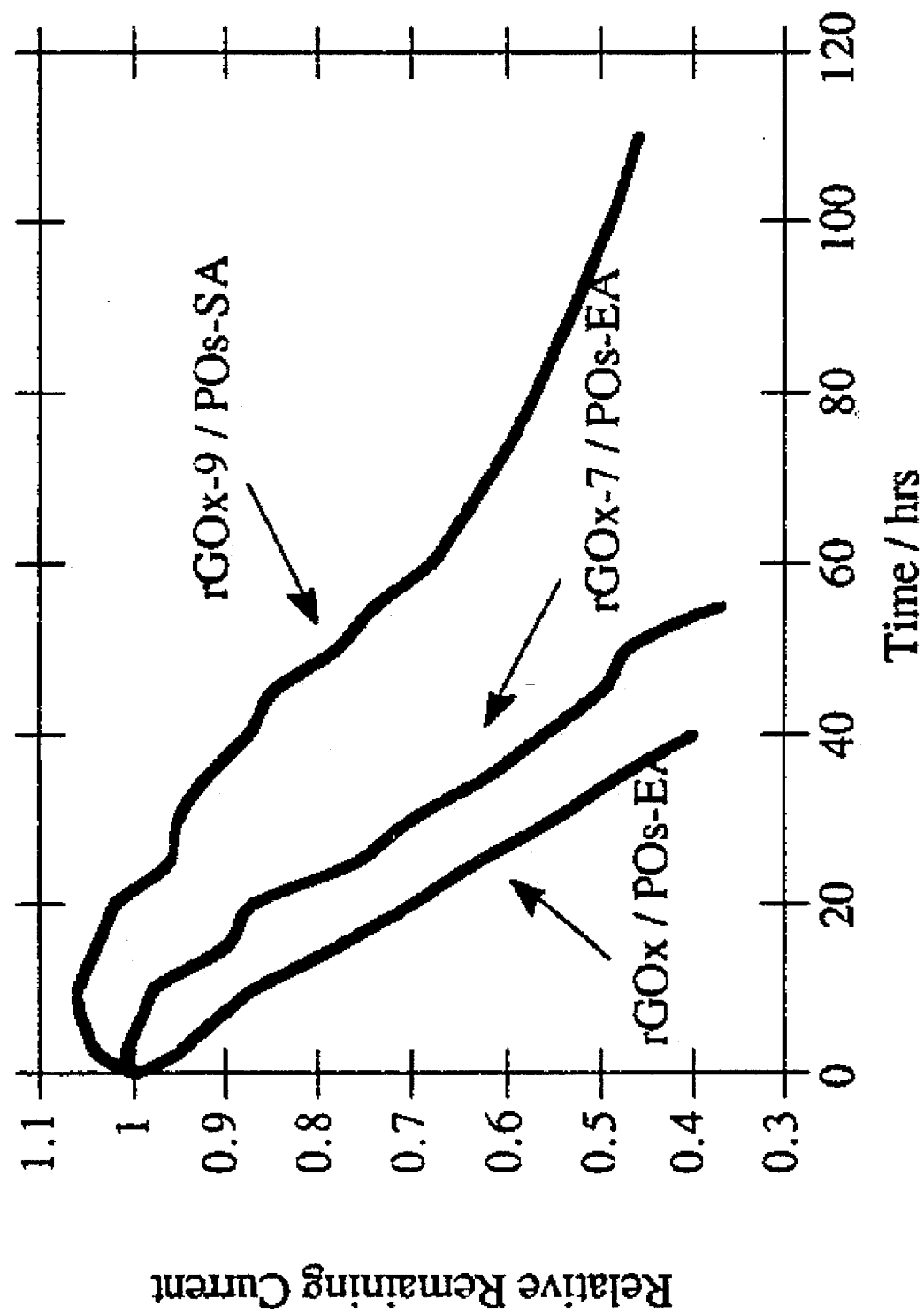
FIG. 10 shows the operational stability of crosslinked enzyme electrodes containing native or chemically modified recombinant glucose oxidases and different redox polyelectrolytes.

Use of the modified rGOx improved the operational stability. FIG. 9 shows the structures of the two crosslinkers used and the possible crosslinking reactions. FIG. 10 shows the time-dependence of the current for three electrodes: Curve (a) was obtained with an electrode modified with rGOx and POs-EA, crosslinked with PEG. The half-life time of this electrode at 37° C. was approximately 35 hours. When the modified rGOx was used (with pI 7) instead of the native enzyme, the half life time was increased to 50 hours (curve b). Curve c represents the decay of an electrode modified with POs-SA and rGOx-9 crosslinked with PAZ. The half life time of this electrode reached 100 hours.

Example 8

Figure 11A:
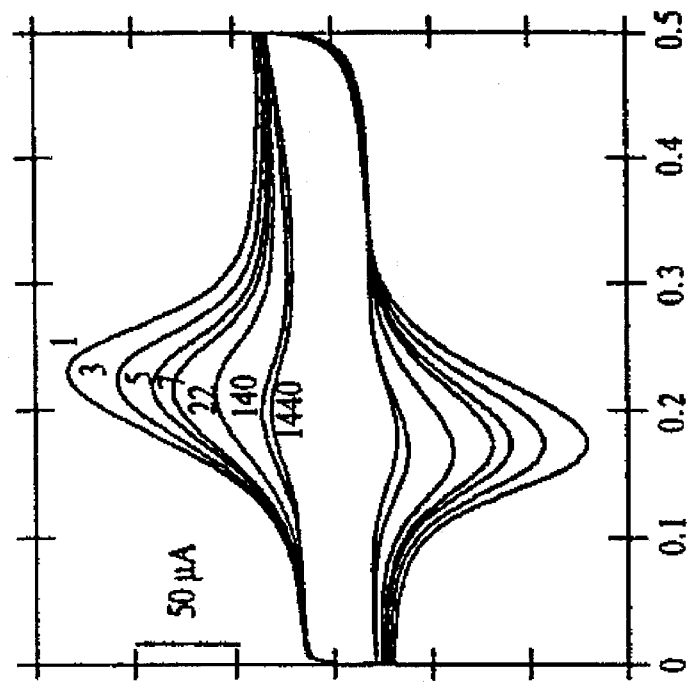
FIGS. 11a and 11a' show, through cyclic voltammograms, progressive adsorption of a cationic redox mediator on a poly(acrylic acid) modified electrode, when the latter is inserted in a solution of said mediator, and the retention of this mediator on such an electrode surface.
Figure 11A:
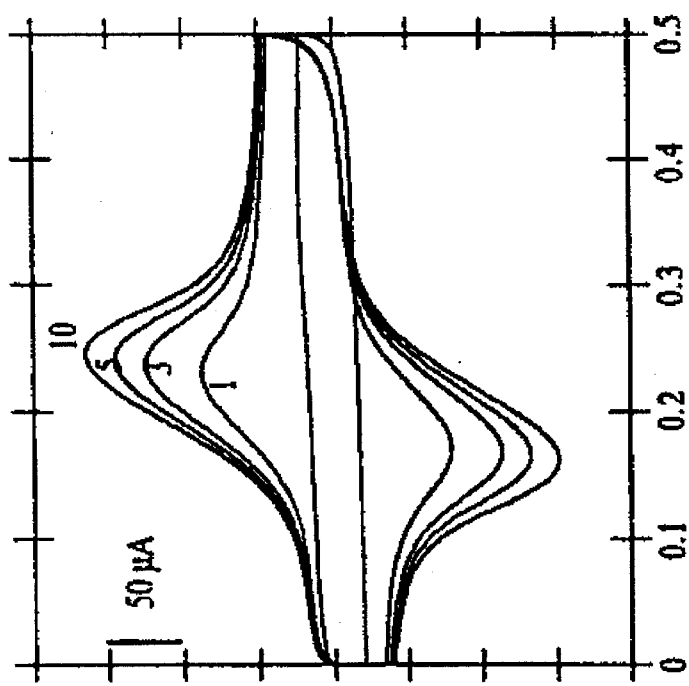
Figure 11C:
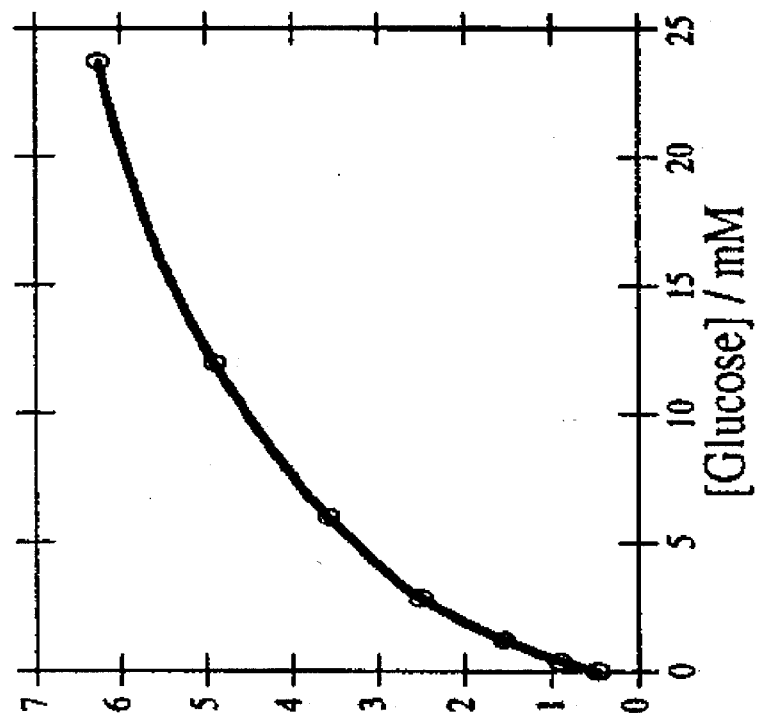
FIG. 11c shows the change of glucose electrooxidation current with glucose concentration for an electrode modified with poly(acrylic acid), aminated recombinant glucose oxidase (isoelectric point 9) and a cationic redox mediator.
Figure 11B:
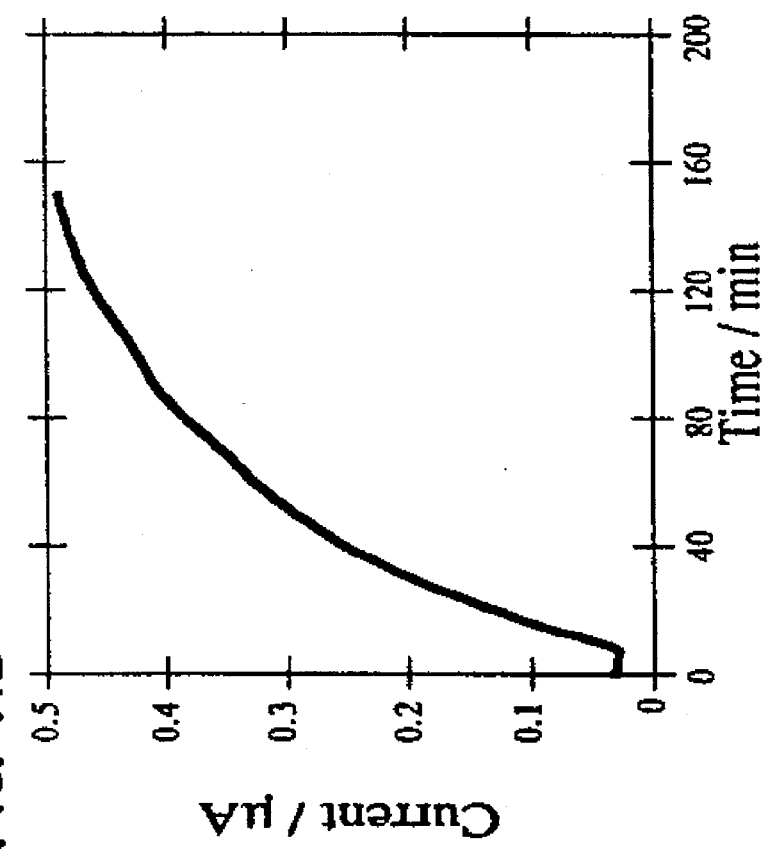

Construction of Enzyme Electrodes by Electrostatic Adsorption of Cationic Mediators and Modified rGOx in a Polyanionic Matrix FIGS. 11a and 11a' show the adsorption and retention of modified enzymes and the cationic mediator [Os(bpy)$_2$(pyOH)Cl]$^{IIIIII}$, where pyOH stands for pyridine-3-propanol, on a polyanionic-matrix modified graphite electrode and the feasibility of using such a system as a glucose sensor. In FIGS. 11a and 11a' the uptake of mediator is represented by the area under 100 mV s$^{-1}$ cyclic voltammograms, the numbers indicating the minutes elapsed after placing the electrode in a 0.66 mM solution of the mediator in physiological buffer. It can be seen that the retained amount of osmium in the matrix is approximately 10$^{-9}$ mol cm$^{-2}$ even after vigorous washing for 24 hours. FIG. 11b shows the uptake of rGOx-9 on the electrode modified with the cationic mediator. The electrode was poised at 0.4 V vs. SCE. The current, measured under anaerobic conditions, was directly related to the activity of adsorbed enzyme and resulted from the electrocatalytic oxidation of glucose by glucose oxidase and the mediator in the matrix. The injected rGOx-9 concentration was 50 μg mL$^{-1}$ or 1.8 units mL$^{-1}$. When the three components were premixed on the electrode surface, the modified electrode responded to glucose as depicted in FIG. 11c.

TABLE 1

Peripheral Amination of Recombinant Glucose Oxidase*

| Reaction number | Periodate Oxidation | | | | Amination | | Final Product | | |
|---|---|---|---|---|---|---|---|---|---|
| | $C_E$ (mg mL$^{-1}$) | $C_{IO}$ (mM) | Time (min) | $n_{ald}$ (ald/enz) | $C_E$ (mg mL$^{-1}$) | $C_{am}$ (M) | pI | Activity (units mg$^{-1}$) | Product name |
| 1 | 5 | 6 | 120 | 130 | 1.4 | 1.5 | 8.5 | 32 | rGOx-8 |
| 2 | 5 | 10 | 120 | 199 | 1.4 | 1.5 | 9.4 | 29 | rGOx-9 |
| 3 | 5 | 20 | 120 | 217 | 1.3 | 1.5 | 9.5 | 24 | rGOx-10 |
| 4 | 5 | 50 | 120 | 145 | 1.3 | 1.5 | 9.5 | 25 | rGOx-10 |
| 5 | 5 | 3 | 60 | 69 | 2.7 | 0.7 | 6.5 | 14 | rGOx-7 |
| 6 | 5 | 3 | 60 | 69 | 4 | 0.07 | 6.5 | 45 | rGOx-7 |
| 7 | 5 | 3 | 60 | 69 | 4 | 0.007 | 6 | 37 | rGOx-6 |
| 8 | 5 | 6 | 7 | 70 | 2 | 0.6 | 7 | 38 | rGOx-C |
| Starting Material | | | | | | | 3.5 | 71 | rGOx |

*$C_E$: enzyme concentration; $C_{IO}$: periodate concentration; $n_{ald}$: number of aldehyde functions per enzyme molecule assuming the MW of rGOx to be 320 kDa and using extinction coefficient for glyceraldehyde $\epsilon = 58,000$ M$^{-1}$ cm$^{-1}$; $C_{am}$: concentration of pentaethylene hexamine used to form Schiff bases.

What is claimed is:

1. A biosensor comprising:
   an electrode having a surface;
   a polyionic polymer; and
   a modified enzyme formed by increasing the number of amine groups covalently bound to a glycosylated redox enzyme such that the pI of the modified redox enzyme is increased by at least 2 pH units with respect to the glycosylated redox enzyme;
   wherein the modified redox enzyme and the polyionic polymer are adsorbed or crosslinked on the surface of the electrode.

2. The biosensor of claim 1, wherein the polyionic polymer is an electron-relaying polymer.

3. The biosensor of claim 2, wherein the polyionic polymer is a polycationic polymer and the modified redox enzyme is a polycationic enzyme.

4. The biosensor of claim 1, wherein the polyionic polymer does not have redox properties and electron transfer is effected by a synthetic mediator adsorbed on the surface of the electrode.

5. The biosensor of claim 4, wherein the synthetic mediator is covalently linked to the modified redox enzyme.

6. The biosensor of claim 1, having a redox potential in the range of −0.05 to +0.3 V (SCE).

7. The biosensor of claim 1, wherein the pI of the modified redox enzyme is increased at least four pH units.

8. The biosensor of claim 1, wherein the pI of the modified redox enzyme is increased at least six pH units.

9. The biosensor of claim 1, wherein the polyionic polymer and the modified redox enzyme are adsorbed on the surface of the electrode by electrophoretic or physico/chemical deposition on the surface.

10. The biosensor of claim 1, wherein the polyionic polymer is polyanionic and the modified redox enzyme is polycationic.

11. The biosensor of claim 1, wherein the polyionic polymer is polycationic and the modified redox enzyme is polycationic.

12. A biosensor comprising:
    an electrode having a surface;
    a polyionic polymer; and
    a modified redox enzyme formed by oxidation of a glycosylated redox enzyme to form an oxidized enzyme and reductive amination of the oxidized enzyme to form amines,
    wherein the polyionic polymer and the modified redox enzyme are adsorbed or crosslinked onto the electrode.

13. A biosensor comprising:
    an electrode having a surface;
    a polyionic polymer; and
    a modified redox enzyme formed by oxidation of oligosaccharide moieties of a glycosylated redox enzyme to form a polyaldehyde-enzyme, reaction of the polyaldehyde-enzyme with an excess of polyamines or amino-polyacids to form Schiff bases, and subsequent reduction of the Schiff bases to form stable, polyaminated or polycarboxylated redox enzymes, wherein the polyionic polymer and the modified redox enzyme are adsorbed or crosslinked on the surface of the electrode.

14. A biosensor comprising:
    an electrode having a surface;
    a polyionic redox polymer and;
    a modified redox enzyme formed by oxidation of oligosaccharide moieties of a glycosylated redox enzyme to form a polyaldehyde-enzyme, reaction of the polyaldehyde-enzyme with an excess of polyamines to form Schiff bases, and subsequent reduction of the Schiff bases to form a stable, polyaminated redox enzyme,
    wherein the polyionic redox polymer and the modified redox enzyme are coated on the surface of the electrode.

15. The biosensor of claim 14, wherein the polyionic redox polymer is poly(vinyl pyridine) derivitized with bis-(bipyridine)osmium.

\* \* \* \* \*

UNITED STATES PATENT AND TRADEMARK OFFICE
CERTIFICATE OF CORRECTION

PATENT NO. : 5,543,326
DATED : Aug. 6, 1996
INVENTOR(S) : Adam Heller, et al.

It is certified that error appears in the above-indentified patent and that said Letters Patent is hereby corrected as shown below:

Column 1, line 39, delete "heir" and insert --their--.

Column 4, line 51, delete "convened" and insert --converted--.

Column 6, line 52, delete "Co$_x$" and insert --GOx--.

Signed and Sealed this

Eighteenth Day of March, 1997

Attest:

BRUCE LEHMAN

*Attesting Officer*   Commissioner of Patents and Trademarks